US012005409B2

(12) United States Patent
Beauducel et al.

(10) Patent No.: US 12,005,409 B2
(45) Date of Patent: Jun. 11, 2024

(54) DEVICE FOR AGITATING AND COLLECTING BIOLOGICAL LIQUID SAMPLES SUITABLE FOR SORTING

(71) Applicant: HORIBA ABX SAS, Montpellier (FR)

(72) Inventors: Florent Beauducel, Montpellier (FR); Philippe Benezeth, Caissargues (FR)

(73) Assignee: HORIBA ABX SAS, Montpellier (FR)

( * ) Notice: Subject to any disclaimer, the term of this patent is extended or adjusted under 35 U.S.C. 154(b) by 329 days.

(21) Appl. No.: 15/775,245

(22) PCT Filed: Nov. 9, 2016

(86) PCT No.: PCT/FR2016/052912
§ 371 (c)(1),
(2) Date: May 10, 2018

(87) PCT Pub. No.: WO2017/081411
PCT Pub. Date: May 18, 2017

(65) Prior Publication Data
US 2018/0326376 A1  Nov. 15, 2018

(30) Foreign Application Priority Data
Nov. 13, 2015 (FR) ...................................... 1560890

(51) Int. Cl.
*G01N 35/00* (2006.01)
*B01F 29/321* (2022.01)
(Continued)

(52) U.S. Cl.
CPC .......... *B01F 29/321* (2022.01); *B01L 3/5025* (2013.01); *G01N 35/00732* (2013.01);
(Continued)

(58) Field of Classification Search
CPC ................ B01F 9/002; G01N 35/0092; G01N 35/00732; G01N 35/1083; G01N 35/0099;
(Continued)

(56) References Cited

U.S. PATENT DOCUMENTS 1,980,930 A * 11/1934 James ........................ B01L 9/06
 211/74
4,124,122 A * 11/1978 Emmitt ..................... B01L 9/06
 422/561
(Continued)

FOREIGN PATENT DOCUMENTS

EP  0726453 A1  8/1996
EP  1655071 A1  5/2006
(Continued)

OTHER PUBLICATIONS

International Search Report issued in International Application No. PCT/FR2016/052912, dated Feb. 21, 2017 (8 pages).

*Primary Examiner* — Benjamin R Whatley
*Assistant Examiner* — Curtis A Thompson
(74) *Attorney, Agent, or Firm* — ArentFox Schiff LLP (57) ABSTRACT

A device for agitating and collecting biological liquid samples comprises an agitator of racks of tubes, a sampling apparatus capable of collecting a biological liquid sample in a tube, and a changer capable of gripping a tube on a rack received in the agitator and moving it to the sampling apparatus. The agitator is capable of agitating at least three racks simultaneously, and the device also comprises a scheduler capable of determining destination data for a tube and destination data for the rack which receives this tube, and of determining for each tube a final location based on the destination data of the tube and the destination data of the racks received in the device, which final location designates a rack, received on the agitator and a position on this rack (Continued)

and can be different from the location of the tube when the rack that received it has been introduced into the device, and arranged to control the changer in order to grip a tube, present it to the sampling apparatus and replace it after sampling at the final location.

14 Claims, 5 Drawing Sheets

(51) Int. Cl.
| | |
|---|---|
| *B01L 3/00* | (2006.01) |
| *G01N 1/00* | (2006.01) |
| *G01N 35/10* | (2006.01) |
| *B01L 9/06* | (2006.01) |
| *B65G 65/00* | (2006.01) |
| *C12Q 1/68* | (2018.01) |
| *G01N 33/96* | (2006.01) |
| *G01N 35/04* | (2006.01) |

(52) U.S. Cl.
CPC ...... *G01N 35/0092* (2013.01); *G01N 35/0099* (2013.01); *G01N 35/1083* (2013.01); *B01L 9/06* (2013.01); *B01L 2300/021* (2013.01); *B65G 65/00* (2013.01); *C12Q 1/68* (2013.01); *G01N 1/00* (2013.01); *G01N 2001/002* (2013.01); *G01N 33/96* (2013.01); *G01N 35/00* (2013.01); *G01N 2035/00524* (2013.01); *G01N 2035/041* (2013.01); *G01N 2035/0412* (2013.01); *G01N 2035/042* (2013.01); *G01N 2035/0472* (2013.01); *G01N 2035/0493* (2013.01); *G01N 35/10* (2013.01); *G01N 2035/1058* (2013.01); *G01N 35/1072* (2013.01)

(58) Field of Classification Search
CPC ........ G01N 35/10; G01N 35/00; G01N 33/96; G01N 1/00; G01N 2035/0412; G01N 2035/1058; G01N 2001/002; G01N 2035/041; G01N 2035/0472; G01N 35/1072; G01N 2035/042; G01N 2035/00524; G01N 2035/0493; B01L 3/5025; B01L 9/06; B01L 2300/021; B65G 65/00

See application file for complete search history.

(56) References Cited

U.S. PATENT DOCUMENTS

| | | | | |
|---|---|---|---|---|
| 5,578,268 | A * | 11/1996 | Champseix | B01F 9/002 422/63 |
| 5,665,309 | A * | 9/1997 | Champseix | G01N 35/04 141/130 |
| 5,985,215 | A * | 11/1999 | Sakazume | G01N 35/026 422/65 |
| 8,986,665 | B2 * | 3/2015 | Fevola | A61Q 19/007 424/70.11 |
| 10,764,922 | B2 * | 9/2020 | Kato | H04W 74/08 |
| 2005/0058574 | A1 * | 3/2005 | Bysouth | G01N 15/0272 422/63 |
| 2005/0169733 | A1 * | 8/2005 | Drynkin | B25J 15/10 414/404 |
| 2009/0142844 | A1 * | 6/2009 | Le Comte | G01N 35/04 436/8 |
| 2010/0291619 | A1 * | 11/2010 | Robinson | C12Q 1/04 435/34 |
| 2014/0037517 | A1 * | 2/2014 | Takai | B01L 9/06 422/562 |
| 2014/0133264 | A1 * | 5/2014 | Kontos | B01F 9/0021 366/214 |
| 2014/0294699 | A1 * | 10/2014 | Akutsu | G01N 35/04 422/551 |
| 2015/0268148 | A1 * | 9/2015 | Hu | G01N 15/05 250/343 |
| 2017/0246600 | A1 * | 8/2017 | Jakobsen | B01F 9/002 |

FOREIGN PATENT DOCUMENTS

| | | |
|---|---|---|
| EP | 2693220 A2 | 2/2014 |
| FR | 2888328 A1 | 1/2007 |
| WO | 93/25885 A1 | 12/1993 |
| WO | WO 03/100382 A1 | 12/2003 |
| WO | WO 2017/081410 A1 | 5/2017 |

\* cited by examiner

DEVICE FOR AGITATING AND COLLECTING BIOLOGICAL LIQUID SAMPLES SUITABLE FOR SORTING

CROSS REFERENCE TO RELATED APPLICATIONS

This application is a 35 U.S.C. 371 National Phase of PCT Application No. PCT/FR2016/052912 filed Nov. 9, 2016, which claims benefit to FR Application No. 1560890 filed Nov. 13, 2015, the disclosure of which is hereby incorporated by reference in its entirety.

The invention concerns the area of collecting biological liquid samples, in particular a body fluid such as blood.

Over the past few decades, blood product analysis units have become increasingly automated. In order to meet the demand for blood tests, requirements with respect to sampling capacity and multi-analysis have exploded. The result is that modern units are assessed based on their analysis speed (number of tubes per hour) and their capacity to carry out multiple types of tests on a single machine.

Developments in this area first favored the processing speed, then the addition of different types of tests. Certain tasks in the sequence to be carried out by the device limit the capacity to increase speed by adding material resources.

It is therefore necessary to agitate the tubes for a certain period of time so that the sample blood product is homogeneous at the time of sampling. Conversely, an agitated sample must not be left immobile for too long prior to sampling, or the benefits of agitation will be lost. In addition, agitation cannot be accelerated beyond a certain speed, or the sample may deteriorate and/or the mixture obtained will be insufficient.

In order to increase speed while taking these limitations into account, agitators with two tubes were proposed, followed by tube supports, also referred to as racks, in order to agitate multiple tubes at the same time. The racks were designed in various configurations until the limits imposed by the agitation and space requirements were reached.

The agitators were then modified so that they could receive two racks simultaneously. In this manner, maintenance of speed during transition between two successive racks was improved, at the same time allowing satisfactory agitation to be maintained.

Devices were progressively automated until the limits of sequential processing of the racks were reached. Nevertheless, these improvements have reached their peak not only in terms of pure speed, but also in terms of management of exceptional cases.

The term exceptional case is understood to mean, for example, a case in which a rack contains only one tube or a tube must be examined urgently without taking into account the racks already processed, or a case in which a tube has already been sampled and testing must be repeated because the result of said testing is suspect (for example, a measurement at the margin of the detection limit).

The situation of a "unique tube" also applies to cases in which a rack contains tubes requiring tests not carried out by the device and in which one single tube on a rack can be effectively analyzed by the device.

This increase in speed is accompanied by the increasing integration of devices within the same installation. Management of the allocation of the tubes between the various devices, and their archiving once the desired tests have been carried out, is a matter of urgency.

To solve this problem, specialized apparatuses called "sorters" have been developed. These apparatuses have the sole function of sorting tube racks in order to group together the tubes that are intended for similar locations, such as archiving.

These devices are very cumbersome, pose significant problems of size and represent a substantial additional cost. In addition to these drawbacks, as soon as the installation changes size, the sorters become too large or too small, thus becoming inadequate or causing a bottleneck.

For this purpose, the invention provides a device for agitating and collecting biological liquid samples comprising an agitator of racks of tubes, a sampling means capable of collecting a biological liquid sample in a tube, and a changer capable of gripping a tube on a rack received in the agitator and moving it to the sampling means.

The agitator is capable of agitating at least three racks simultaneously, and the device further comprises a scheduler capable of determining destination data for a tube and destination data for the rack which receives this tube, and of determining for each tube a final location based on the destination data of the tube and the destination data of the racks received in the device, which final location designates a rack received on the agitator and a position on this rack and can be different from the location of the tube when the rack that received it has been introduced into the device, and arranged to control the changer in order to grip a tube, present it to the sampling means and replace it after sampling at said final location.

This device is particularly advantageous because it completely changes the way in which management of the tubes is configured. Specifically, in the prior art, tubes were always analyzed sequentially according to their position in the racks, and racks were always processed sequentially as well. The devices were seen as automated mechanical units intended to process the racks inserted by the user as quickly as possible.

The invention radically changes the manner in which sampling devices operate by allowing processing that is no longer strictly sequential, but is indexed so as to maintain full speed regardless of the situation in question. Specifically, the scheduler makes it possible to process the tubes on the racks in an intelligent order depending on the general processing status of the device, but also based on the steps and tests to be carried out on the tubes, or based on other parameters.

This is no longer a case of automated mechanical units processing tubes one after the other as quickly as possible; the invention provides an intelligent unit that adapts to operating conditions in order to maintain the maximum speed regardless of said conditions.

According to various embodiments, the device can have one or more of the following characteristics:
- the scheduler is arranged, for a given tube, to choose the final location from among the free locations on a rack that has the same destination data as the given tube,
- the scheduler is arranged to determine, as a final location on a given rack, the first empty location on the given rack,
- the scheduler is arranged to reset the destination data associated with a given rack when the latter is introduced into the device,
- when no rack presents the same destination data as a tube gripped by the changer, the scheduler is arranged to assign the destination data associated with this tube to a rack to which no destination data is associated,
- the scheduler is arranged to control the changer in order to shift vertically a tube received in a rack according to the destination data associated with this tube, the scheduler is arranged to control the changer in order to output a rack from the device and to arrange it in an output position that varies as a function of the destination data associated with the rack, the scheduler is arranged to output a rack from the device having empty locations, in response to a user command or in response to the passing of a chosen duration, after a rack having empty locations has been output, the scheduler is arranged to introduce into the device a rack having an at least equal number of empty locations, and the device further comprises a zone for connection to a conveyor of racks.

The invention also concerns a method for agitating and sampling of tubes comprising the following steps:

a. insertion of at least one rack, receiving at least one tube containing at least one biological liquid, into a device for agitating and collecting biological liquid samples, b. determination of destination data for each tube in the device and of destination data for each rack which receives one of these tubes, c. for each tube received in the device, determination of a final location based on the destination data of the tube and the destination data of the racks received in the device, which final location designates a rack received in the device and a position on this rack, and can be different from the location of the tube when the rack that received it has been introduced into the device, d. collection of biological liquid samples in each tube received in the device, e. placement of the tube in its final location after step d).

Other characteristics and advantages will be clarified by reading the following description, taken from examples given on an illustrative rather than a limitative basis, which refers to drawings showing the following.

The drawings and the following description for the most part contain definite elements. They can serve not only to improve understanding of the present invention, but to contribute towards defining it if necessary.

Figure 1:
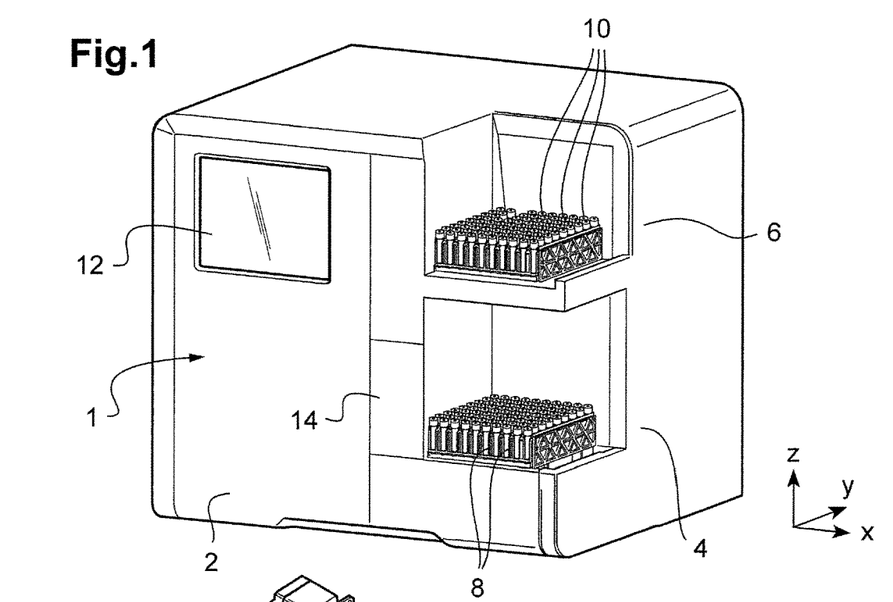
FIG. 1 shows a perspective view of a device according to the invention.

FIG. 1 shows a perspective view of a device 1 according to the invention. A locator XYZ makes it possible to identify the various orientations of the figures on which it is shown.

The device 1 comprises a housing 2 of generally cuboid shape that has two recesses respectively for a loading tray 4 and an unloading tray 6. The trays 4 and 6 make it possible respectively to insert and retrieve the racks 8 of tubes 10 containing the biological liquids and blood products that the device 1 is to sample and analyze. The racks 8 are arranged parallel to one another on the trays 4 and 6 along their length, i.e. along the Y axis.

In the example shown in FIG. 1, the racks are inserted into the machine from right to left on the loading tray 4, i.e. the rack 8 farthest to the left of the loading tray 4 is inserted first, and the one farthest to the right is inserted last. For the unloading tray 6, the situation is reversed: it is the rack 8 farthest to the right that has been ejected first, while the rack 8 farthest to the left is the one ejected most recently. In the example described here, because of its arrangement inside the device 1, the loading tray 4 is located in the lower part of the device 1, while the unloading tray 6 is located in the upper part. Alternatively, the functions of the trays 4 and 6 could be reversed, or the trays could play roles depending on the operating mode of the device 1, being used for loading or unloading of the racks 8 depending on the situation.

Figure 2:
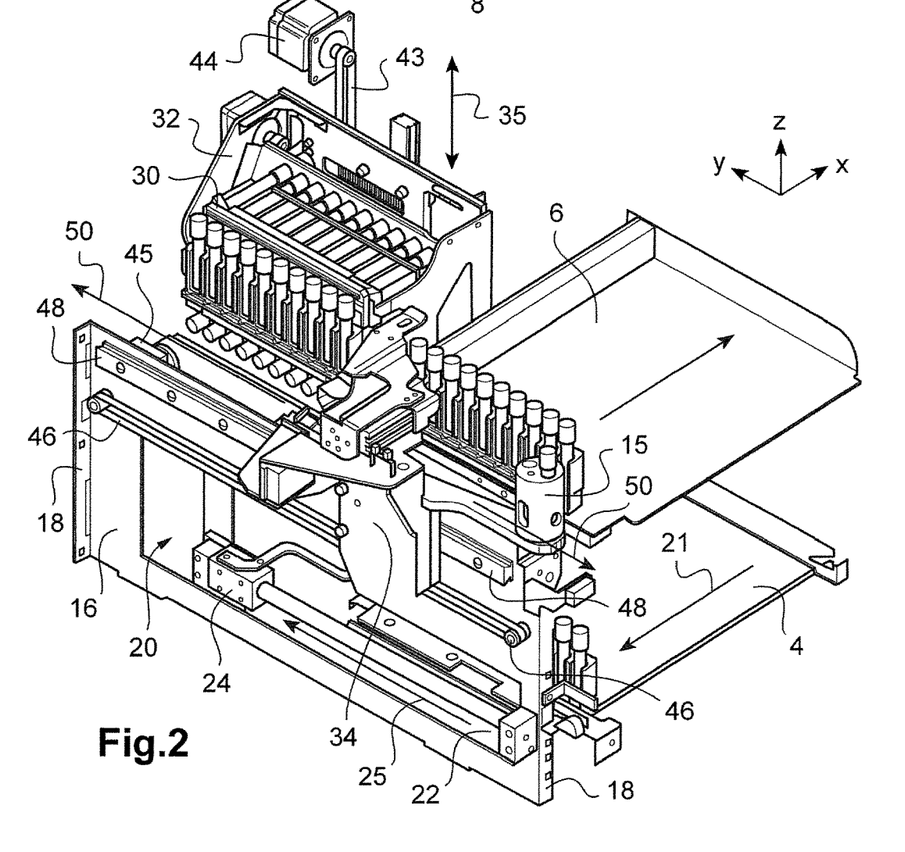
FIG. 2 shows a perspective view of a portion of the components of the device of FIG. 1.
Figure 8:
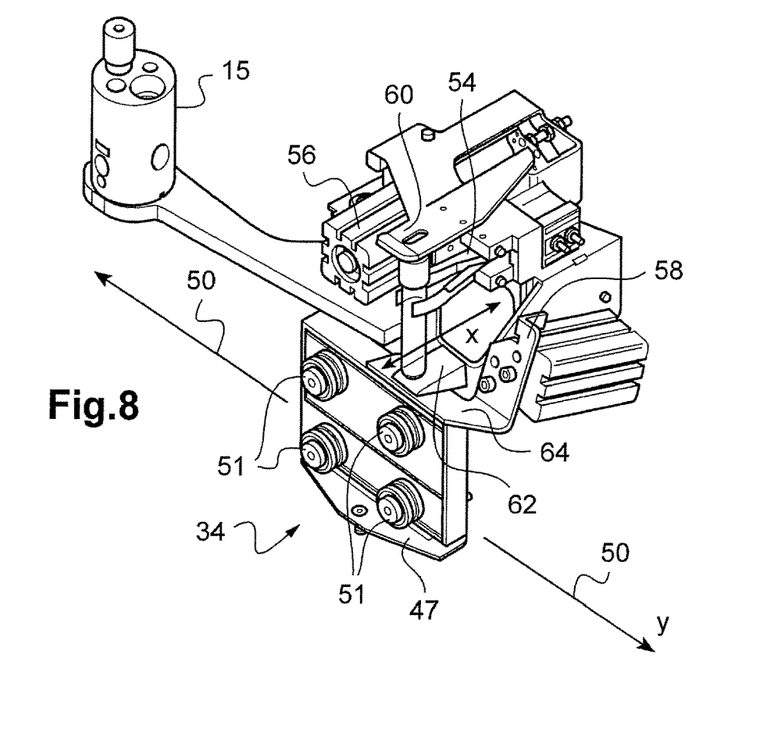
FIG. 8 shows a perspective view of the changer of FIG. 2.

The housing 2 also has a screen 12 that makes it possible to control the device 1 and monitor the operating status thereof. Finally, the housing 2 has a hatch 14 that allows the insertion of a "priority tube." A priority tube is a single tube that a user wishes to process on a priority basis with respect to the others. As can be seen in FIGS. 2 and 8, this tube is received in a barrel 15 that is part of the device 1. The hatch 14 can also be used for inserting tubes whose processing is incompatible with the use of a rack, for example tubes for pediatric use.

FIG. 2 shows a perspective view of a portion of the components contained inside the housing 2 of the device 1. As can be seen in this figure, the device 1 receives a wall 16 that chiefly runs in direction Y and is located approximately at the level of the end of the loading tray 4. The wall 16 has two arms 18 that allow it to be fixed in place on the housing 1 and an opening 20 through which a loader 22 can be seen.

The loader 22 is attached to the wall 16 approximately at the level of the loading tray 4 on the side opposite thereto. When a rack 8 is pushed in the direction of the arrow 21 from the tray 4, it is received directly by the loader 22. The loader 22 comprises an actuator 24 capable of moving in the direction Y that controls a projection (not shown) through the opening 20 that pushes a rack 8 received in the loader 22 in the direction indicated by the arrow 25 toward the inside of the device 1, as will be seen below. In some non-limiting examples, the arrow 25 may indicate a first axis.

The device 1 also comprises an agitator 30, a lifting mechanism 32, and a changer 34. The agitator 30 has the function of mixing the racks of tubes 8 it receives by rotation around an axis approximately parallel to Y. In some non-limiting examples, the rotation axis of the agitator may be interchangeably referred to as a second axis.

Figure 4:
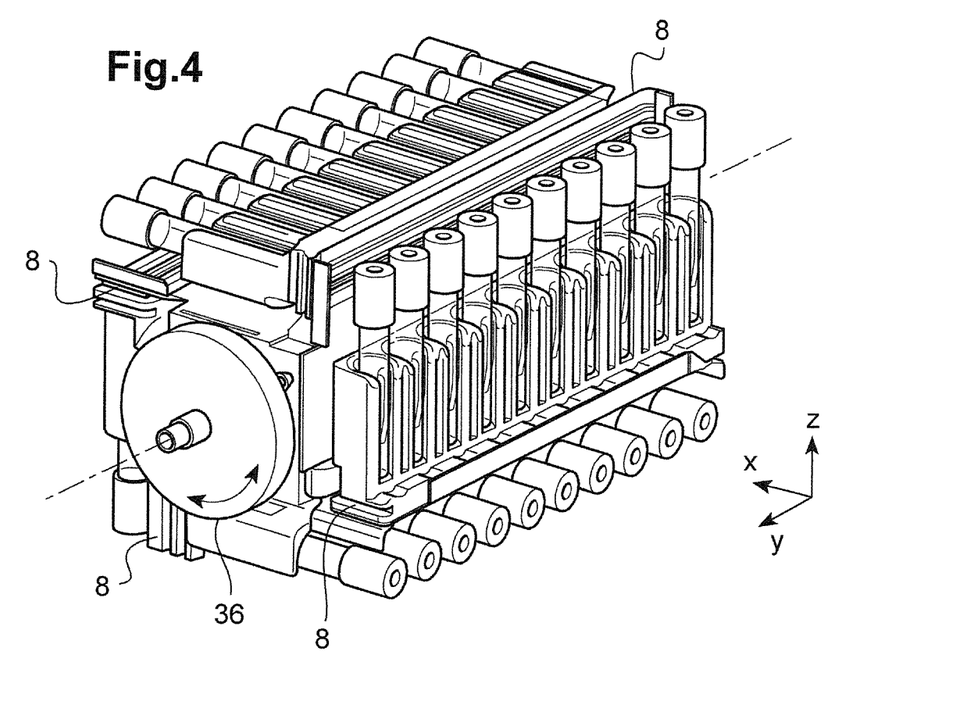
Figure 5:
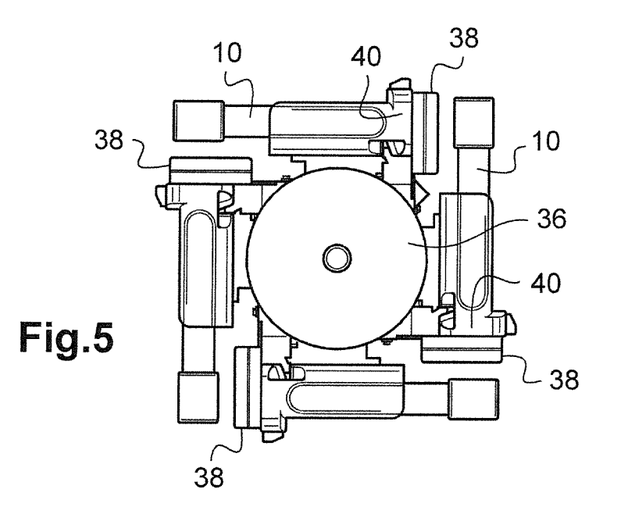

As can be seen in FIGS. 4 and 5, the agitator 30 can receive 4 racks 8, each disposed at an angle of approximately 90° with respect to the others. Alternatively, the agitator 30 could be arranged to receive only 3 racks 8 or more than 4 racks. The agitator 30 comprises a motor 36 that is configured to apply rotation that allows mixing of the contents of the tubes 10 received on the racks 8 it supports.

As will be seen below, the motor 36 can also be activated in order to position a selected rack 8 opposite the changer 34. In order to receive the racks 8, the agitator 30 comprises four supports 38, each having a guide 40 extending in the Y direction. The supports 38 are connected to the motor 36 such that rotation of the latter drives rotation of the supports 38 and the racks 8 they receive.

Figures 6, 7:
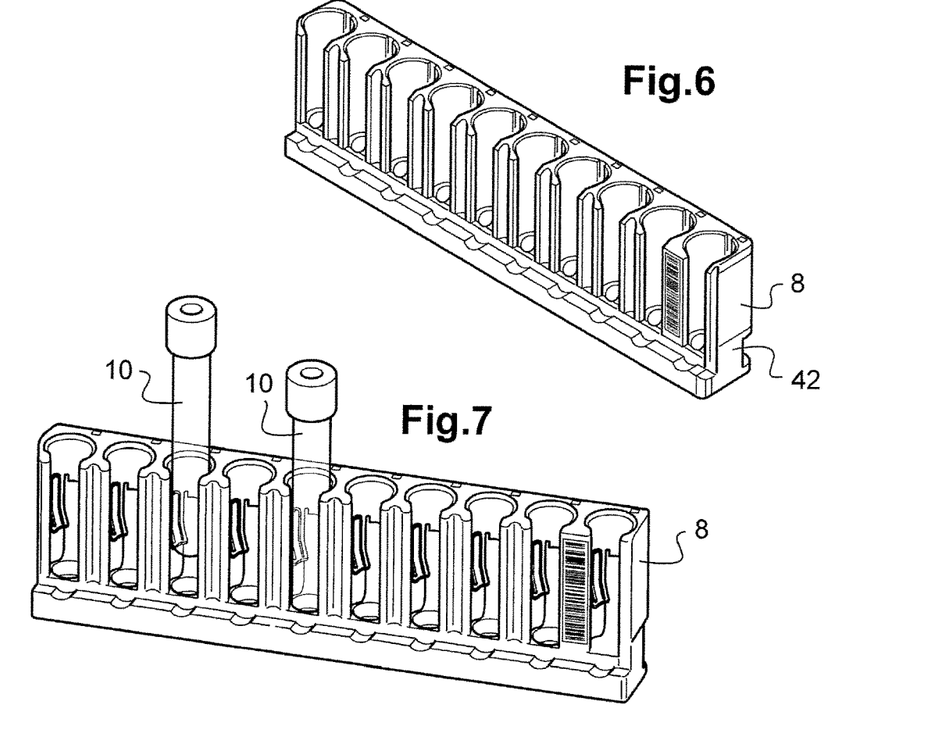

As can be seen in FIGS. 6 and 7, the racks 8 have a T-shaped base 42 that fits into one of the guides 40 of the agitator 30. In this manner, in order to insert a rack 8, one need only place the desired support 38 of the agitator 30 opposite the loader 22, and the actuator 24 is activated in order to push the rack 8 into place in the corresponding guide 40.

The agitator 30 is displaced inside the device 1 by the lifting mechanism 32 as indicated by the arrow 35 in FIG. 2. The lifting mechanism 32 causes the agitator 30 to move along the Z axis, which may be alternatively referred to throughout the disclosure as a third axis, between a receiving position and an unloading position. In some examples, the receiving position may be a low position in which the agitator 30 can receive a rack 8 of the loader 22 and the unloading position may be a high position in which the changer 34 can sample a tube 10 on a rack 8 and/or a high position in which one or more trays can be unloaded onto unloading tray 6. The lifting mechanism 32 is driven by a belt 43 and a motor 44.

FIG. 8 shows a perspective view of the changer 34 along an axis that is a mirror image of the view in FIG. 2.

The changer 34 comprises a motor 45 that drives a belt 46 that is connected to an attachment portion 47. The changer 34 has wheels 49 that are received in a rail 48 visible in FIG. 2 mounted on the wall 16. In this manner, the changer 34 moves along the Y axis as indicated by the arrow 50.

Figure 3:
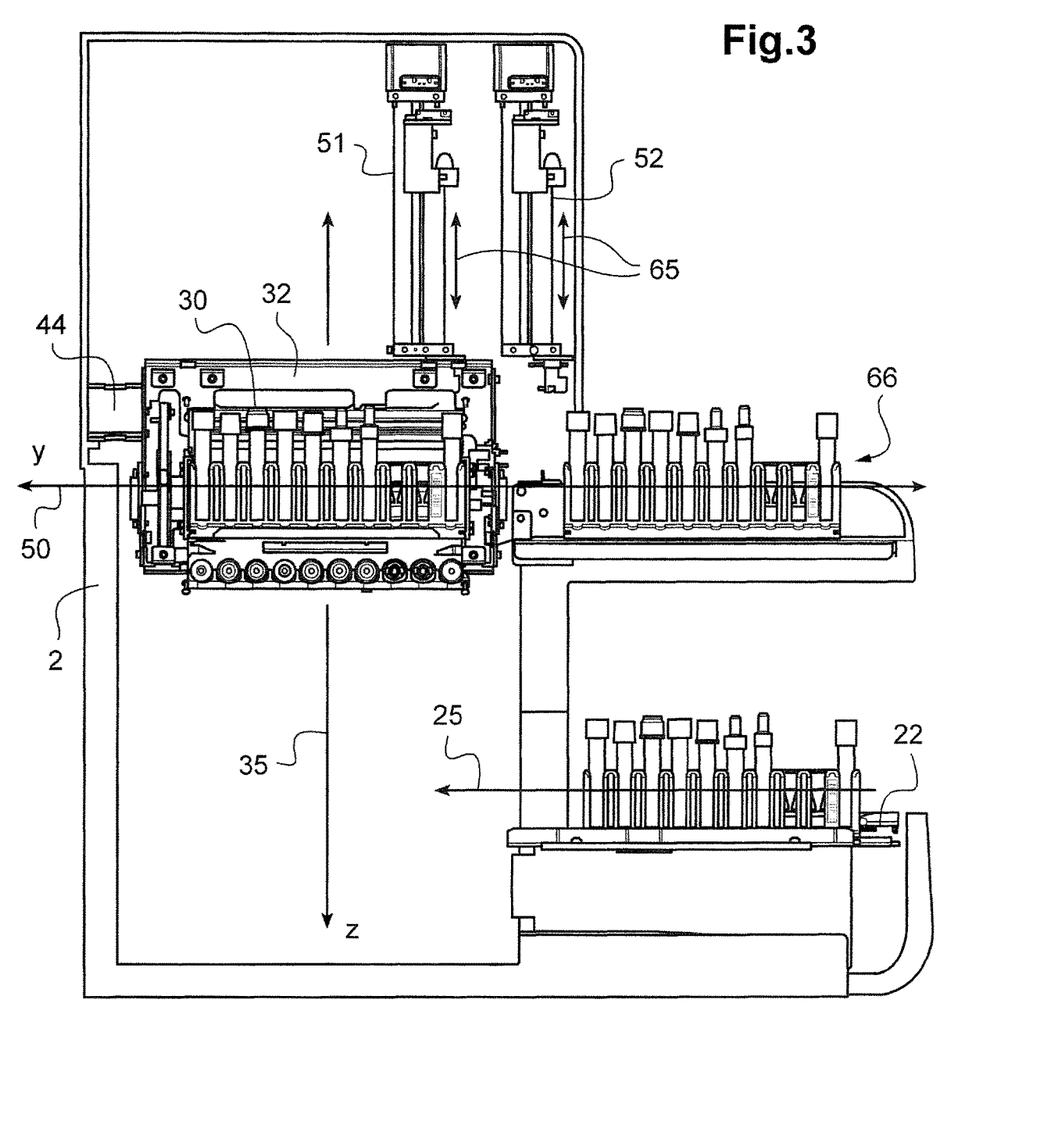
FIG. 3 shows a side view of the inside of the device of FIG. 1, FIGS. 4 and 5 show a perspective view and a side view respectively of an agitator shown in FIGS. 2 and 3, FIGS. 6 and 7 show a perspective view of a tube rack of FIGS. 4 and 5 respectively with and without tubes.

The main function of the changer 34 is the sampling of a tube 10 from a rack 8 received in the agitator 30 and the bringing of this tube 10 toward a first sampling means 51 or a second sampling means 52 (visible in FIG. 3).

In order to carry out sampling of the tubes 10, the changer 34 comprises a clamp 54 that is moved along the X axis by means of a driver 56. In order to identify the tube 10 to be sampled, the changer 34 uses a sensor 58 that reads a bar code or another means of optical identification carried by the tubes 10. The clamp 54 could also be replaced by another gripping means, for example a vacuum nozzle, a magnetic device, etc. The sensor 58 could also be different, and could for example be an RFID sensor.

Finally, the changer 34 comprises an upper stop 60 and a lower stop 64 that limit the movement of the tube during the insertion and withdrawal of the sampling needle, as well as a pusher 62. The pusher 62 makes it possible to eject a rack 8 of the agitator 30 toward the unloading tray 6.

In order to bring a tube 10 of the agitator 30 toward one of the sampling means 51 and 52, the lifting mechanism 32 moves the agitator 30 in a high position at the level of the changer 34, and the motor 36 of the agitator 30 positions the desired rack 8 opposite the changer 34. The changer 34 then moves along the Y axis until the tube 10 sought is identified by means of the sensor 58. Once the tube 10 has been identified, the driver 56 moves the clamp 54, which grips the tube 10, and the lifting mechanism 32 causes the agitator 32 to descend in direction Z such that the tube 10 is withdrawn from the rack 8. The changer 34 is then moved in direction Y below the first sampling means 51 or the second sampling means 52. Once the changer 34 has stopped, the needle of the sampling means moves along the Z axis as indicated by the arrows 65 in order to carry out sampling in the tube 10. Finally, by means of a series of reverse steps, the tube 10 is put back in the rack 8 on the agitator 30.

In order to withdraw a rack 8 from the agitator 30, the changer 34 is moved all the way left along the Y axis according to the view in FIGS. 2 and 3. The lifting mechanism 32 then moves the agitator 30 in a high position at the level of the changer 34, and the motor 36 of the agitator 30 positions the rack sought 8 opposite the changer 34. Finally, the changer 34 is moved to the right along the Y axis, with the pusher 62 progressively pushing the rack 8 outside the support 38 that receives it until it reaches an unloading zone 66 of the unloading tray 6, and a driver not shown moves the withdrawn rack 8 along the X axis as indicated by the arrow 67 in order to withdraw the rack 8 from the device 1.

All of the steps are coordinated by a scheduler that can be configured in the form of a computer program. The function of the scheduler is to coordinate the loader 22, the agitator 30, the lifting mechanism 32, and the changer 34 as well as the sampling means 51 and 52 in order to insert the racks 8, agitate them, and carry out sampling.

In the example described here, the scheduler is integrated into the housing of the device 1. Alternatively, the scheduler could be in a remote configuration and be operated from a computer or a controller outside the housing of the device 1 and in communication with the latter either by wire or wirelessly. In addition, such a computer or controller could control a plurality of devices 1 to which it is connected, with said devices being independent of one another.

When a rack 8 is loaded into the agitator 30, it is moved by the lifting mechanism 32 to the level of the changer 34, which uses the sensor 58 to determine which tubes 10 are present on the rack 8 and the tests required for these tubes.

The scheduler thus knows exactly which tubes are present on the racks 8 and can specify a sampling and testing sequence that makes it possible to optimize the speed of the device 1.

Specifically, if a priority tube is inserted via the hatch 14, the scheduler can "pause" the sequence in progress and prepare for sampling of the priority tube as soon as sampling of the tube in progress is completed and said tube has been put back in its rack.

Figure 9:
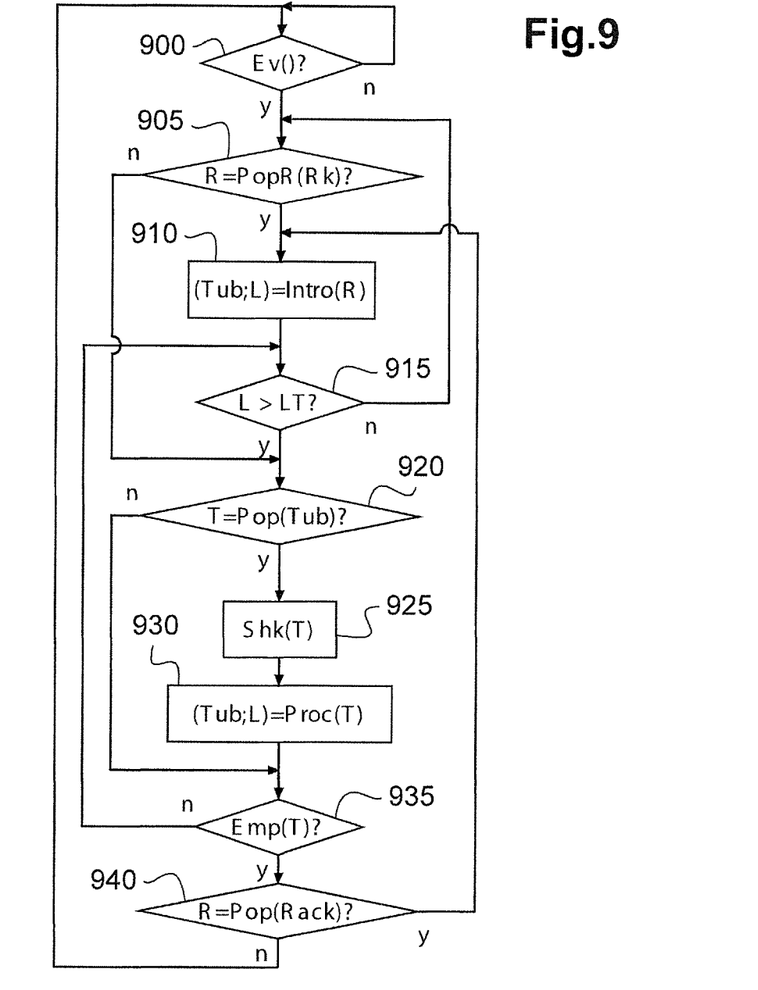
FIG. 9 shows an example of a function implemented by the scheduler.

FIG. 9 shows an example function implemented by the scheduler.

This figure shows an operating loop of the scheduler that begins with a step 900 in which a function Ev( ) tests for the presence of a testing launch event.

When such an event is detected, a function PopR( ) is executed in a step 905. The function PopR( ) receives as an argument an Rk list. The Rk list contains the identifiers of the racks 8 of tubes 10 currently received by the device 1. In the example described here, the racks 8 are arranged by order of priority in the Rk list, such that the first rack 8 is the one that must be treated on a priority basis, and so forth.

The management of the Rk list and the insertion of the racks 8 therein can be controlled by the scheduler or be automated. In the example described here, the racks 8 received on the loading tray 4 are classified in order of proximity to the entrance of the device 1, while when a priority rack or a priority tube is inserted, it is placed at the top of the Rk list. Other methods of managing the Rk list may also be used.

The function PopR( ) unstacks the Rk list, and the resulting rack identifier 8 is stored in a variable R. Next, in a step 910, a function Intro( ) is executed. The function Intro( ) receives the variable R as an argument and returns a Tub list and a variable L.

In the example described here, the function Intro( ) instructs the device 1 to insert the rack 8 whose identifier is given the variable R and to proceed with mixing of the tubes 10 it carries.

In the example described here, this insertion comprises the reading of labels affixed to the tubes 10 allowing determination of the tubes 10 in question, as well as the required tests. The identifiers of the tubes 10 are stored in the Tub list for subsequent testing. The reading of the tubes 10 also allows determination of the required duration of the tests to be carried out for the rack 8 designated by the variable R, and this required time is added to the variable L, which receives the estimated time in order to analyze all of the tubes loaded into the device 1.

The function Intro( ) is capable of modifying the Tub list based on the course of processing since the last execution of the function Intro( ) based on one or more of the following criteria:

the type of tests to be carried out on the newly inserted tubes, the priority status of the one or plurality of newly inserted tubes, the degree of agitation of the tubes in the device, the origin of the rack of newly inserted tubes (tray, priority tube, etc.), the residence time of each tube present in the device.

Other criteria can be taken into account according to the circumstances.

Next, in a step 915, a test compares the variable L to a threshold LT. The threshold LT corresponds to the estimated duration required for agitating the tubes of a rack 8. Specifically, if the total duration of the remaining tests is less than this duration (on the order of two minutes in the example described here), it is preferable to load a new rack in order to agitate said rack as quickly as possible and ensure the maximum operating speed of the device 1.

If L is less than LT, then step 910 is repeated. In the opposite case, testing of a tube is initiated. For this purpose, in a step 920, a test determines whether the Tub list is empty by means of a function PopT( ) that receives the Tub list as an argument.

If the Tub list is not empty, then the function PopT( ) determines which tube must be tested next. For example, in the case of a priority rack or a priority tube inserted in the step 910, the Tub list can receive the identifiers of these tubes at a location such that they will be processed first as soon as their agitation is completed. In this scenario, the Tub list is quite simply unstacked, and the identifier of the corresponding tube is returned in a variable T.

In other embodiments, the function PopT( ) can be more complex and can decide based on intrinsic and/or extrinsic algorithms the next tube to be analyzed.

Next, in a step 925, a function Shk( ) determines whether the tube designated by the variable T has been sufficiently agitated. If this is not the case, additional agitation is carried out.

The tube designated by the variable T is then analyzed in a step 930 by a function Proc( ). The function Proc( ) instructs the device 1 to search for the tube with the identifier T on its rack in order to bring it to one of the two sampling means 51 and 52 and to put it back in its rack once the testing has been carried out. In order to search for the tube with the identifier T, the device 1 can order reading of the labels of the tubes on the rack in question or use an intermediate table associating each tube received in the device 1 with a given location on one surface of the agitator 30. In the example described here, the sampling means 51 is dedicated to direct tests, while the sampling means 52 is dedicated to repeating tests.

The function Proc( ) also updates the Tub list, either by deleting the identifier T or by replacing it if it is necessary to repeat the test. The variable L is also updated accordingly by subtracting from it the duration of the testing that was planned for the tube with the identifier T.

Finally, in a step 935, a function Emp( ) determines whether the Tub list is empty. If this is not the case, the loop starts again with step 915 in order to determine whether a new rack must be loaded. If not, in a step 940, a step identical to step 910 is carried out. When there is no longer a rack available, all of the tests have been carried out, and the device 1 starts over by waiting for the next event in step 900. If not, the loop starts again with step 910 for inserting this rack.

If the agitator 30 has rack-receiving holders, one of them can be left permanently empty in order to serve as a buffer used for temporarily storing a tube as needed.

The fact that the agitator 30 can receive at least three racks 8 makes it possible to ensure optimum speed if it is necessary to repeat a test (also referred to as Rerun/Reflex). In this manner, continuity of speed is ensured even if the three racks only contain one "useful" tube.

Specifically, before undergoing sampling, the tubes must be agitated to an extent sufficient to ensure the homogeneity of the mixture in each tube. This means that when a rack is inserted into the device, the tubes must first be agitated. However, this step requires the equivalent of 4 sampling steps. Accordingly, when two racks can be received, a certain continuity of speed can be ensured by beginning to agitate the tubes of the second rack while the last tubes of the first rack are being sampled.

Nevertheless, in the case of a priority tube or a step of the type Rerun/Reflex, the speed may drop long enough for the tubes to be properly agitated. The third rack makes it possible to continue processing one or two racks while simultaneously agitating the priority tube or the tube of a step of the type Rerun/Reflex. Therefore, the latter are processed as quickly as possible while maintaining the maximum operating speed of the device.

If the agitator 30 receives 4 supports or more, this opens up new possibilities, such as the use of a rack buffer described above, or the possibility of permanently leaving a support empty in order to allow use of the "priority rack," i.e. no longer a single tube, but an entire rack of tubes that will be sampled and analyzed on a priority basis.

Finally, the device 1 can also receive a second agitator similar to the agitator 30. This allows the use of additional buffers, and the lifting mechanism 32 and the changer 34 allow the transfer of one rack to another on the same agitator or between the two agitators.

By means of the new paradigm proposed by the invention, it becomes possible to achieve an actual speed of 120 samplings per hour, even when using priority tubes or with racks having only one useful tube each. In addition to the improved actual rate, the configuration of the device according to the invention opens up new possibilities in handling of tests, as it becomes possible to determine the most rapid sampling route independently of the composition of the racks and their order of insertion into the device 1. Based on the dimensions selected for the components of the device, the speed could be increased, for example to 240 samplings per hour or more.

Within the context of the invention, the applicant conducted further mechanical and functional testing of the components of the device in order to achieve the smoothest operation possible.

This led the applicant to specify step cycles of 15 seconds and to specify the following steps:

a.—loading of a rack from the forward tray and identification of this rack and the tubes it receives, b.—agitation, c.—verification of the identifier of a tube, gripping of this tube, supplying it for sampling, and putting the tube back in place, d.—ejection of a rack toward the forward tray.

Steps a. through d. make it possible to simply manage the interactions in a device not connected to a conveyor and not capable of sorting the tubes and/or racks. The scheduler is configured to manage these steps in an order that makes it possible to optimize the operating speed of the device.

The applicant also discovered that these steps could be extended in order to automate the connection of the device to a conveyor (reference no. 1000 in FIG. 10), thus making it possible to send them to another device for agitating and collection (reference no. 1100 in FIG. 10), which could be in accordance with device 1 according to the invention or different therefrom, and in order to automate sorting of the tubes 10 and/or the racks 8 of the tubes 10 for subsequent automated or manual processing.

In this case, new steps can be specified for management by the scheduler:
- e. loading of a rack from the conveyor and identification of this rack,
- f. verification of the identifier of a tube, gripping of this tube, supplying it for sampling, then putting this tube back in place, and simultaneous loading of a rack from the waiting area of the conveyor,
- g. verification of the identifier of a tube, gripping of this tube, supplying it for sampling, then putting this tube back in place, and simultaneous ejection of a rack toward the waiting area of the conveyor,
- h. agitation and identification of a rack,
- i. ejection of a rack toward the conveyor,
- j. ejection of a rack with displacement on the forward tray,
- k. vertical shifting of one or a plurality of tubes of a rack and ejection of this rack on the forward tray with or without displacement of the rack (e.g., the vertical height of one or a plurality of tubes with respect to the base of a respective rack may be altered according to the tube destination data so that the one or plurality of the tubes protrudes further from the rack with respect to the remaining plurality of tubes),
- l. verification of the identifier of a tube, gripping of this tube, supplying it for sampling, and putting the tube back in a location other than its original location (rack and/or position on the rack),
- m. verification of the identifier of a tube, gripping of this tube, supplying it for sampling, then putting this tube back in a location other than its original location (rack and/or position on the rack), and simultaneous loading of a rack (from the waiting area of the conveyor or from another location),
- n. verification of the identifier of a tube, gripping of this tube, supplying it for sampling, and then putting this tube back in a location other than its original location (rack and position on the rack), simultaneous ejection of a rack (toward the waiting area of the conveyor or toward another location), and
- o. verification of the identifier of a tube, gripping of this tube, and putting the tube back in a location other than its original location (rack and position on the rack).

Figure 10:
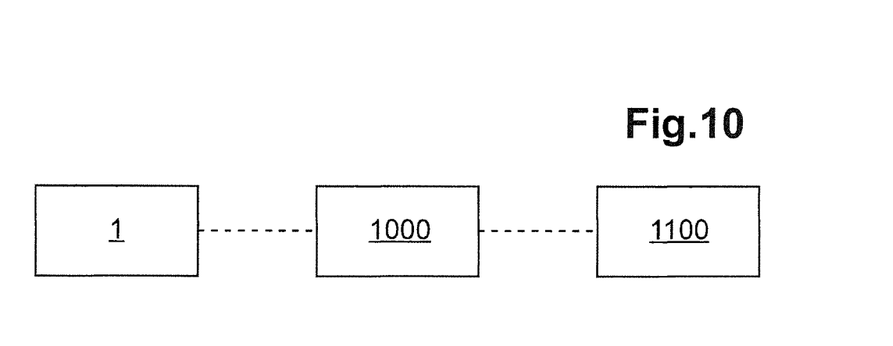
FIG. 10 shows a schematic view of an apparatus comprising a plurality of devices, at least one of which is in accordance with FIG. 1.

Steps e. through i. make it possible to manage the connection of the device of the invention to a more complex system in a testing laboratory. In this case, the device is capable of receiving the tubes 10 and/or the racks 8 of other devices 1100 in the system. This transfer is carried out by a conveyor 1000 that brings the tubes 10 and/or the racks 8 to a dedicated waiting area of the device 1.

Steps j. and k. make it possible to manage the tubes and/or racks for manual sorting. Specifically, an operator who sees at the outlet a vertically displaced tube (e.g., a height of with respective rack to the base of the respective rack as shown in FIG. 7) and/or a displaced rack will know that the latter must be subjected to separate processing, whether this be an additional testing or a repeated testing. Of course, the dimensions of the device (length of the tray, height of the rack outlet) must be adapted accordingly.

Steps a. through k. do not require any adaptation of the logic of the device described above. The insertion of a rack (function Intro( ) of FIG. 9) and the processing of a tube (function Proc( ) of FIG. 9) and/or a rack (function Empt( ) of FIG. 9) can be adjusted so as to insert one or more of steps a. through k. as needed.

For their part, steps l. through o. make it possible to carry out fully automated sorting of the tubes and/or the racks. Specifically, as a tube can be put back in a location different from its original location, this makes it possible to rearrange the group of tubes on different racks in order to take into account the tests remaining to be carried out.

This has several advantages. The sorting devices, whether they are dedicated to storage or circulation of the tubes between multiple devices of the same system, are extremely costly, take up a lot of space, and must be precisely dimensioned relative to the system.

Moreover, if the system changes in size (addition of other devices or reduction in size), the sorting device becomes unsuitable or must even be replaced. In the invention, the dedicated sorting device is simply eliminated, because sorting is internalized. This means lower costs, less space required, less design time (dimensioning), and increased flexibility of scale (regardless of the size of the system, sorting is integrated).

Finally, as sorting is integrated, one can save considerable time in filling the racks. Specifically, it is no longer necessary to prepare the racks by grouping together the tubes for which similar tests are to be carried out in order to pre-sort the tubes. Users may place the tubes in the racks in bulk, regardless of the tests to be conducted, and the device will optimize the distribution of the tubes in the racks.

This type of automated processing is made possible by two characteristics.

The first characteristic is the capacity of the agitator to agitate at least three racks simultaneously, allowing permanent use of one of the three racks as an adjustment destination.

In this manner, as soon as it is determined that a tube must undergo testing different from that of the tubes of its original rack after the current testing, said tube is put back on the adjustment rack after testing. As soon as it is determined that another tube must undergo the same testing, it is also put back on the rack, and so on, until the adjustment rack is full or a time threshold has been exceeded, after which the adjustment rack is withdrawn from the device, toward the conveyor if there is one, or with displacement on the tray in order to indicate to the user the destination of this rack.

In classic operation of the device, the total number of "empty" locations on the racks received (i.e., the number of locations not receiving a tube) is constant, as the tubes that are moved onto another rack or to a location other than their original location leave the latter empty. It remains the case that the adjustment racks are ejected as soon as they are full and are replaced by another full incoming rack.

When the adjustment rack is withdrawn at the request of the user or if a time threshold is exceeded, an empty rack must be inserted into the device in order to restore the capacity for adjustment.

Generally speaking, each additional rack managed by the agitator allows management of a different adjustment destination. Four racks thus make it possible to manage two adjustment destinations, and the addition of a second agitator will make it possible to increase the number of adjustment destinations.

The second characteristic is a change in management of the logic of the device. Specifically, in the case described with reference to steps a. through k., the device is completely independent of the rest of the chain, as a rack will come back out the same way it went in, although the tubes it contains will not necessarily be processed in their order in the rack or another rack may be treated on a priority basis. To put it another way, the device constitutes a closed universe not influenced by other devices, even when it is connected to a conveyor.

In the case of steps l. through o., the device is a link in a chain formed by the system. As such, the management of the device is affected by the general status of the system.

Thus, when a rack is inserted into the device, the device reads the data relating to each of the tubes of this rack, derives from this the destination data for each tube, and updates the list of steps to be carried out for each tube. The destination data indicate the next device to which the tube must be transported after processing, or indicate storage if there is no additional testing. In the example described here, the destination data are determined based on the identifier of the tube by accessing a local or remote database. Alternatively, they can be part of the data read on the tube.

Next, when the time comes to carry out testing of a given tube, i.e. when the device instructs the clamp to grip the tube on the rack, a new reading of the data pertaining to the tube is carried out in order to determine whether the destination data of the tube after the current testing are identical to those of the rack that receives them. If this is the case, step c., f., or g. is carried out depending on what is provided for optimizing speed. If not, step l., m., or n. is carried out.

Initially, no rack has destination data. It is at the time of sampling of the first tube the rack receives that it may be assigned destination data. Specifically, according to the invention, when no rack has destination data identical to that of the tube, this destination data is assigned to the oldest rack.

Alternatively, the racks could be assigned destination data based on the destination data of the tubes they receive and on the destination data of the other racks that are already loaded at the time of loading the rack into the device.

In this manner, as the tubes are processed, the arrangement thereof and their distribution on the racks loaded into the device are modified. For example, when a tube has been put back in a rack different from its original rack, if the following tube of the original rack is put back in the original rack, it will be placed not in its original location but in the location left empty by the preceding tube.

In a similar manner, if a tube of a given rack is not to be tested but has destination data different from that of the rack that receives it, specific movement of the tube by the clamp can be carried out (step o.). This is also the case if a tube received on a rack already loaded into the device has its testing modified and no longer corresponds to the analysis or tests for which the device is intended.

Among the steps described above, step o. is the only one capable of affecting speed in that it does not provide for any testing. Nevertheless, this situation should be extremely rare in practice, and it cannot be avoided.

It thus appears that although the device functions according to the same principles as those set forth above and makes it possible to obtain similar advantages, its logic is different, as external events may affect its operation.

For example, the user may decide to add a supplementary test not planned at the outset for a tube that is already in the system. In this case, the tube will most probably be moved toward a destination adjustment rack during one of its processing runs. In addition, all of the subsequent tubes will also be moved to a location different from their additional location. Despite this, the speed will remain at the maximum level by means of the device of the invention.

The examples given for implementing steps l. through o. were described with reference to a system comprising a plurality of devices connected by a conveyor. Nevertheless, they can be fully combined with steps j. and k. even without a conveyor. Specifically, the racks having selected destination data can be displaced on tray 4 or 6 according to a distance characteristic of the destination in question. Moreover, the corresponding destination data can be displayed nearby for each rack.

In the above, the duration of the steps was set at 15 seconds, a duration that provides a good compromise between the granularity of the steps and the efficiency of scheduling, specifically in view of the desired rate of 120 samplings per hour. Alternatively, other durations could be selected based on trade-offs and the desired rates.

In general, each time a rack that has been inserted empty into the device is retrieved "by force," i.e., at the request of the user, or after a time threshold is exceeded, whether this occurs toward a conveyor or toward a tray, it must be replaced. This replacement can be carried out manually or automatically (for example via the conveyor).

The device described above is configured to carry out a certain number of tests after sampling of the tubes. Alternatively, the device could be limited to sampling alone, and the analyzer could be remote from the unit.

Although the above description has pertained to blood products, the invention can be applied in the processing of all types of biological liquids, particularly body fluids.

The invention claimed is:

1. A device for agitating and collecting biological liquid samples, comprising:
   a loader for loading racks containing sample tubes onto an agitator, wherein each rack of the racks has a plurality of tube positions to receive the sample tubes therein;
   the agitator receives the racks via the loader and along a first axis, and is configured to rotate about a second axis and agitate at least three racks of the racks simultaneously, wherein the agitator is further configured to translate along a third axis between a receiving position for receiving the racks to an unloading position for unloading the racks wherein the unloading position of the agitator is higher than the receiving position of the agitator:
   a sampling apparatus capable of collecting a biological liquid sample in a respective sample tube,
   a changer configured to grip the respective sample tube from one of the plurality of tube positions of the racks received by the agitator, the changer being capable of moving the respective sample tube to the sampling apparatus, and
   a controller comprising a scheduler, wherein the controller is configured to control the scheduler to determine tube destination data and rack destination data,
     wherein the scheduler determines a final tube location based on the tube destination data and the rack destination data received by the device,
       wherein in a case that the final tube location of the respective sample tube is designated as a first rack on the agitator and as a second position of the plurality of tube positions of the first rack on the agitator that is different from an initial position of the respective sample tube in the racks received by the agitator, the scheduler controls the changer to grip the respective sample tube and remove the respective sample tube from the first initial position, present the respective sample tube to the sampling apparatus, and replace the respective sample tube after sampling to said second position, wherein the scheduler is configured to control the changer to alter a vertical height of the respective sample tube with respect to a base of the first rack according to the tube destination data so that the respective sample tube protrudes further from the first rack than a second tube in the first rack, when the first rack is unloaded.

2. The device according to claim 1, wherein the scheduler is configured to choose the final tube location from among free positions that have a same tube destination data.

3. The device according to claim 2, wherein the scheduler is configured to determine, as the final tube location, a first sequentially empty position on the first rack.

4. The device according to claim 1, wherein the scheduler is configured to reset the rack destination data when a respective rack is introduced into the device.

5. The device according to claim 1, wherein the scheduler is configured to control the changer to eject the first rack from the device, and to arrange the first rack in the unloading that varies as a function of the rack destination data.

6. The device according to claim 1, wherein the scheduler is configured to eject a rack of the at least three racks that has empty positions from the device, in response to a user command or in response to a passing of a chosen duration.

7. The device according to claim 5, in which, after a rack of the at least three racks having empty positions has been ejected, the scheduler is arranged to introduce into the device a new rack having an at least equal number of empty positions.

8. The device according to claim 1, further comprising a zone for connection to a convey of racks.

9. The device of claim 1, further comprising a pusher for unloading one or more racks from the agitator onto an unloading tray.

10. The device of claim 9, wherein the loader is configured to load one or more racks onto the agitator from a loading tray.

11. A process for agitating and sampling tubes, comprising:
   a. inserting at least three racks, each of the at least three racks comprising a plurality of holders configured to hold a number of tubes containing biological liquid, into a device for agitating and collecting biological liquid samples via a loading tray of the device, wherein a loading device provides the at least three racks to an agitator along a first axis and the agitator is configured to rotate about a second axis,
   b. determining, via a scheduler, tube destination data for at least one tube, and a rack destination data for the at least one tube,
   c. determining a final tube location for the at least one tube based on the tube destination data and the rack destination data, wherein the final tube location includes a final rack designation and a final tube position, wherein, in a case that the tube destination data for the at least one tube is designated as different from an original tube position, the final tube position is different from the original tube position wherein the tube destination data designates both a position of the at least one tube in a respective rack and a vertical height of the at least one tube with respect to a base of the respective rack of the at least three racks when the at least three racks were originally inserted into the device,
   d. moving the agitator from a loading position to a sampling position along a third axis wherein the sampling position of the agitator is higher than the loading position of the agitator;
   e. collecting a sample of liquid in the at least one tube,
   f. placing the at least one tube in the final tube location after step e), and
   g. unloading the respective rack containing the at least one tube onto an unloading tray.

12. The process of claim 11, wherein the first axis and the second axis are parallel.

13. The process of claim 12, wherein the third axis is perpendicular to the first axis and the second axis.

14. A device for agitating and collecting biological liquid samples, comprising:
   a loader for loading racks containing sample tubes onto an agitator, wherein each rack of the racks has a plurality of tube positions to receive the sample tubes therein;
   the agitator receives the racks via the loader and along a first axis, and is configured to rotate about a second axis and agitate at least three racks of the racks simultaneously, wherein the first axis and the second axis are parallel and the agitator is further configured to translate along a third axis between a receiving position for receiving the racks to an unloading position for unloading the racks, wherein the third axis is perpendicular to the first axis and the second axis;
   a sampling apparatus capable of collecting a biological liquid sample in a respective sample tube,
   a changer configured to grip the respective sample tube from one of the plurality of tube positions of the racks received by the agitator, the changer being capable of moving the respective sample tube to the sampling apparatus, and
   a controller comprising a scheduler, wherein the controller is configured to control the scheduler to determine tube destination data and rack destination data,
   wherein the scheduler determines a final tube location based on the tube destination data and the rack destination data received by the device,
   wherein in a case that the final tube location of the respective sample tube is designated as a first rack on the agitator and as a second position of the plurality of tube positions of the first rack on the agitator that is different from an initial position of the respective sample tube in the racks received by the agitator, the scheduler controls the changer to grip the respective sample tube and remove the respective sample tube from the first initial position, present the respective sample tube to the sampling apparatus, and replace the respective sample tube after sampling to said second position, wherein the scheduler is configured to control the changer to alter a vertical height of the respective sample tube with respect to a base of a respective the first rack according to the tube destination data so that the respective sample tube protrudes further from the first rack than a second tube in the first rack, when the first rack is unloaded.

* * * * *